US012661254B2

(12) United States Patent (10) Patent No.: US 12,661,254 B2

Sitt et al. (45) **Date of Patent: \*Jun. 23, 2026**

(54) DEVICES, SYSTEMS, AND METHODS FOR THE TREATMENT OF CLOGGED GLANDS OF THE EYE

(71) Applicant: PLEASE ME LLC ROTH 401(K) PLAN F/B/O EDDIE SITT AND CAROLYN SITT, Brooklyn, NY (US)

(72) Inventors: Carolyn Sitt, Brooklyn, NY (US); Eddie Sitt, Brooklyn, NY (US)

(73) Assignee: Please Mc LLC Roth 401(K) Plan F/B/O Eddie Sitt and Carolyn Sitt, Brooklyn, NY (US)

( \* ) Notice: Subject to any disclaimer, the term of this patent is extended or adjusted under 35 U.S.C. 154(b) by 1291 days.

This patent is subject to a terminal disclaimer.

(21) Appl. No.: 17/388,975

(22) Filed: Jul. 29, 2021

(65) Prior Publication Data

US 2021/0353453 A1 Nov. 18, 2021

Related U.S. Application Data

(63) Continuation of application No. 17/142,872, filed on Jan. 6, 2021, now Pat. No. 11,135,087, which is a (Continued)

(51) Int. Cl.
*A61F 7/00* (2006.01)

(52) U.S. Cl.
CPC ...... *A61F 7/007* (2013.01); *A61F 2007/0004* (2013.01); *A61F 2007/0078* (2013.01)

(58) Field of Classification Search
CPC .............. A61F 7/007; A61F 2007/0004; A61F 2007/0071
See application file for complete search history.

(56) References Cited

U.S. PATENT DOCUMENTS 2,635,175 A \* 4/1953 Wilson .................... A61F 7/007
219/528
3,173,419 A 3/1965 Dubilier et al.
(Continued)

FOREIGN PATENT DOCUMENTS

CN 111228036 A 6/2020
CN 211356221 U 8/2020
(Continued)

OTHER PUBLICATIONS

International Search Report and Written Opinion issued in International Patent Application No. PCT/US2023/032695, dated Dec. 18, 2023.

(Continued)

*Primary Examiner* — Joseph A Stoklosa
*Assistant Examiner* — Adam J Avigan
(74) *Attorney, Agent, or Firm* — Foley & Lardner LLP

(57) ABSTRACT

A system for treating clogged glands of the eye includes a heated eye mask, an electrical cord, and a controller. The heated eye mask includes an outer layer of surface material, an inner layer of surface material, and a graphene heating element. The graphene heating element is disposed between the outer and inner layers of surface material in a therapeutic region of the heated eye mask. The therapeutic region of the heated eye mask extends along the Meibomian glands of the eye. The graphene heating element is encapsulated by an electrically insulating cover. A thermally conductive material evenly distributes heat across the therapeutic region of the heated eye mask. The electrical cord provides power to the heated eye mask. The controller is provided on the electrical cord for controlling the heated eye mask to heat to one of at least four pre-set temperature levels.

13 Claims, 8 Drawing Sheets

Related U.S. Application Data continuation-in-part of application No. 16/913,870, filed on Jun. 26, 2020, now abandoned.

(60) Provisional application No. 62/866,846, filed on Jun. 26, 2019.

(56) References Cited

U.S. PATENT DOCUMENTS

| | | | |
|---|---|---|---|
| 4,736,088 A * | 4/1988 | Bart | A61F 13/00 |
| | | | 219/211 |
| D324,734 S | 3/1992 | Burgess | |
| 5,769,806 A | 6/1998 | Radow | |
| 6,193,740 B1 | 2/2001 | Rodriguez | |
| 6,438,964 B1 | 8/2002 | Giblin | |
| 6,714,821 B1 | 3/2004 | Duda et al. | |
| D631,500 S | 1/2011 | Schenk | |
| 8,632,578 B2 | 1/2014 | Korb et al. | |
| 9,655,771 B1 * | 5/2017 | Sauls | A61F 7/02 |
| 9,795,502 B1 * | 10/2017 | Kopes | A61F 7/007 |
| D861,772 S | 10/2019 | Lian | |
| D862,568 S | 10/2019 | Holtz et al. | |
| D907,224 S | 1/2021 | Wang | |
| D911,429 S | 2/2021 | Guo | |
| 11,135,087 B2 | 10/2021 | Sitt et al. | |
| D945,000 S | 3/2022 | Mcmahon | |
| D949,954 S | 4/2022 | Sitt et al. | |
| 11,576,630 B1 | 2/2023 | Maiman | |
| D999,270 S | 9/2023 | Liu | |
| 11,844,638 B1 | 12/2023 | Maiman | |
| D1,013,767 S | 2/2024 | Huang | |
| D1,016,130 S | 2/2024 | Zhu | |
| D1,028,066 S | 5/2024 | Kanakis | |
| 12,053,311 B2 | 8/2024 | Maiman | |
| 2007/0272246 A1 | 11/2007 | Ulm | |
| 2008/0104743 A1 | 5/2008 | Ng | |
| 2008/0286208 A1 | 11/2008 | Korb | |
| 2009/0287282 A1 | 11/2009 | Biser et al. | |
| 2012/0222192 A1 | 9/2012 | Carey et al. | |
| 2014/0303700 A1 | 10/2014 | Hinkle | |
| 2014/0331383 A1 | 11/2014 | Bially | |
| 2015/0012073 A1 | 1/2015 | Devine | |
| 2015/0012074 A1 | 1/2015 | Devine | |
| 2015/0290028 A1 | 10/2015 | Isserow et al. | |
| 2016/0299543 A1 * | 10/2016 | Brooks | H05B 3/145 |
| 2017/0014300 A1 | 1/2017 | Dippo et al. | |
| 2017/0266035 A1 | 9/2017 | Kuo | |
| 2018/0055691 A1 * | 3/2018 | Renaud | A61F 7/007 |
| 2019/0060158 A1 | 2/2019 | Grenon et al. | |
| 2019/0358087 A1 | 11/2019 | Fuller | |
| 2020/0129327 A1 | 4/2020 | Grant et al. | |
| 2020/0405532 A1 | 12/2020 | Sitt et al. | |
| 2021/0121320 A1 | 4/2021 | Sitt et al. | |
| 2021/0169682 A1 | 6/2021 | Alvarez et al. | |
| 2021/0353453 A1 | 11/2021 | Sitt et al. | |
| 2023/0013787 A1 | 1/2023 | Sitt et al. | |

FOREIGN PATENT DOCUMENTS

| | | |
|---|---|---|
| EM | 015016369-0001 | 4/2023 |
| GB | 2 561 707 A | 10/2018 |
| GB | 6 272 283 | 3/2023 |
| JP | 3221547 U | 6/2019 |
| KR | 10-1778114 B1 | 9/2017 |
| KR | 10-2019-0085531 A | 7/2019 |
| WO | WO-2006/061596 A1 | 6/2006 |
| WO | WO-2018/044877 A1 | 3/2018 |
| WO | WO 2019-193000 A1 | 10/2019 |

OTHER PUBLICATIONS

Long, Yin et al., "Wearable and implantable electroceuticals for therapeutic electrostimulations", Advanced Science, Feb. 19, 2021 (published online), vol. 8, article No. 2004023, pp. 1-22.

Non-Final Office Action issued in co-pending U.S. Appl. No. 16/913,870, dated Mar. 11, 2024.
International Search Report and Written Opinion issued in International Patent Application No. PCT/US2022/011173, dated Apr. 21, 2022.
Extended European Search Report issued in European Patent Application No. 22736995.6, dated Nov. 25, 2024.
Aroma Season Eye Compress Heated Eye Mask for Dry Eyes, posted at amazon.com, posting date by Jan. 19, 2020, [online], [sited visited Sep. 6, 2023]. Available from Internet, URL: https://www.amazon.com/dp/B0841KC4GD? (Year: 2023).
Aroma Season Heated Eye Mask, posted at amazon.com, posting date by Mar. 23, 2019, [online], [site visited Dec. 8, 2021]. Available from Internet, URL: https://www.amazon.com/dp/B07LBL172C/ (Year: 2019).
Carefor Heated Sleep Eye Mask, posted at amazon.com, posting date by Jan. 16, 2023[online], [sited visited Sep. 15, 2023]. Available from Internet, URL: https://www.amazon.com/dp/B0BM95S7D1 (Year: 2023).
Carefor Heated Sleep Eye Mask, posted at amazon.com, posting date by Jul. 7, 2023[online], [sited visited Sep. 15, 2023]. Available from Internet, URL: https://www.amazon.com/dp/B0BM95JD9G (Year: 2023).
Cheroo Heated Eye Mask, posted at amazon.com, posting date by Feb. 14, 2021, [online], [sited visited Dec. 8, 2021]. Available from Internet, URL: https://www.amazon.com/Lavender-Weighted-Compress-Adjustable-Blepharitis/dp/B08T97LNP6/ref=cm_cr_arp_d_product _top?ie=UTF8 (Year: 2021).
Dr.Prepare Heated Eye Mask, posted at amazon.com, posting date by Jan. 14, 2020, [online], [sited visited Sep. 6, 2023]. Available from Internet, URL: https://www.amazon.com/dp/B083TYGF38 (Year: 2023).
Drop of DiviniTi Heated Eye Mask for Dry Eyes, posted at amazon.com, posting date by May 19, 2019, [online], [sited visited Sep. 6, 2023]. Available from Internet, URL: https://www.amazon.com/dp/B07QYQ6Q9V?th=1 (Year: 2023).
Drop of DiviniTI Heated Eye Mask for Dry Eyes, posted at amazon.com, posting date unknown [online], [sited visited Sep. 15, 2023]. Available from Internet, URL: https://www.amazon.com/dp/B08S55D5RQ (Year: 2023).
Ghukn Heated Eye Mask Cordless, posted at amazon.com, posting date by Dec. 3, 2022 [online], [sited visited Sep. 15, 2023]. Available from Internet, URL: https://www.amazon.com/dp/B0BNX2N3DM (Year: 2023).
HIM Microwave Activated Warm Eye Compress, posted at amazon.com, posting date by Oct. 13, 2020, [online], [sited visited Sep. 6, 2023]. Available from Internet, URL: https://www.amazon.com/dp/B08JCK6DWC (Year: 2023).
Heyedrate Heated Eye Mask, posted at amazon.com, posting date unkown, [online], [sited visited Sep. 6, 2023]. Available from Internet, URL: https://www.amazon.com/dp/B078YCFZDB (Year: 2023).
Meisenhome Heated Eye Mask, posted at amazon.com, posting date by Nov. 13, 2020, [online], [sited visited Dec. 8, 2021]. Available from Internet, URL: https://www.amazon.com/MEISENHOME-Blepharitis-Treatment-Flaxseed-Chalazion/dp/B08TTGYKV6/ref=cm_cr_arp_d_product_top?ie=UTF8&th=1 (Year: 2020).
Morliden Heated Eye Mask for Dry Eyes, posted at amazon.com, posting date by Feb. 10, 2021, [online], [sited visited Dec. 8, 2021]. Available from Internet, URL: https://www.amazon.com/Natural-Flaxseed-Compress-Adjustable-Temperature/dp/B08TTYLHQL/ref=cm_cr_arp_d_product_top?ie=UTF8&th=1 (Year: 2021).
Strico Heated Eye Mask, posted at amazon.com, posting date by Jan. 20, 2021, [online], [sited visited Sep. 6, 2023]. Available from Internet, URL: https://www.amazon.com/dp/B08T93WCKY (Year: 2023).
Topoint Heated Eye Mask Moist Heat Eye Compress, posted at amazon.com, posting date by Oct. 26, 2018, [online], [sited visited Sep. 6, 2023]. Available from Internet, URL: https://www.amazon.com/dp/B07JQ41HKB (Year: 2023).
Aroma Season Heated Eye Mask with Flaxseed, Warm Eye Compress for Dry Eyes to Unclog Glands, Relieve Dry Eye Syndrome, MGD, Stye and Blepharitis (Blue). available on Amazon.com, date

(56) References Cited

OTHER PUBLICATIONS first available Mar. 4, 2019 [online], [site visited Apr. 26, 2025], Available from the internet URL: https://www.amazon.ca/Flaxseed-Therapy-Relieve-Syndrome-Blepharitis/dp/B07LBL172C/ref=asc_df_B07LBL172C/?gad_source=1&hvadid=706827340304&hvdev=m&hvdvcmdl&hvlocint&hvlocphy=9000660&hvnetw=g&hvpone&hvpos&hvptwo&hvqmt&hvrand.

Aroma Season Warm Compress for Dry Eyes, Heated Eye Mask Microwave Moist Hot Therapy Flaxseed Filling for Stye Chalizion Blepharitis Migraine (Red). available on Amazon.com, date first available May 4, 2020 [online], [site visited Apr. 16, 2025], Available from the internet URL: https://www.amazon.ca/dp/B0841KC4GD/ref=sspa_dk_detail_2?pf_rd_p=516c2169-755e-413a-a38a-68230f4ab66f&pf_rd_r=CRPQHBKFA4NN4F16VS74&pd_rd_wg=KcqLP&pd_rd_w=cDWjv&content-id=amzn1.sym.516c2169-755e-413a-a38a-68230f4ab66f&pd_rd_r=.

Cavoilu Cooling Sleep Mask w/Gel Eye Mask, available on Amazon.com, date first available Feb. 18, 2022 [online], [site visited Mar. 11, 2025], Available from the internet URL: https://www.amazon.com/Cavoilu-Sleeping-Puffiness-Compress-Blackout/dp/BO9SQ5QDHOQ (Year: 2022).

Product Checker. "Ikea Stjärnanemon Eye mask". YouTube Video, Mar. 27, 2023, https://www.youtube.com/watch?v=b3djV17Sb70.

Youige Sleep Mask for Women Men, available on Amazon.com, date first available Dec. 1, 2019 [online], [site visited Mar. 11, 2025], Available from the internet URL: https://www.amazon.com/dp/B08271TCKG/ (Year: 2019).

Non-Final Office Action on U.S. Appl. No. 16/913,870 DTD Jul. 21, 2022.

Search Report issued in co-pending European Patent Application No. 20830965.8, dated Jun. 9, 2023.

Non-Final Office Action issued in co-pending U.S. Appl. No. 16/913,870, dated Jun. 2, 2023.

Final Office Action issued in co-pending U.S. Appl. No. 16/913,870, dated Feb. 1, 2023.

* cited by examiner

MEIBOMIAN GLAND

MEIBOMIAN GLAND

800

801

POSITION A HEATED EYE MASK ON AN EYE REGION

802

SET A TEMPERATURE AND/OR LENGTH OF TIME FOR THE THERAPY SESSION

803

CONNECT THE HEATED EYE MASK TO A POWER SOURCE

804

MAINTAIN THE HEATED EYE MASK ON THE EYE REGION AT THE SET TEMPERATURE FOR A DESIRED AMOUNT OF TIME

DEVICES, SYSTEMS, AND METHODS FOR THE TREATMENT OF CLOGGED GLANDS OF THE EYE

CROSS-REFERENCE TO RELATED PATENT APPLICATIONS

This application is a continuation of U.S. patent application Ser. No. 17/142,872 filed Jan. 6, 2021, which is a continuation-in-part of U.S. patent application Ser. No. 16/913,870 filed Jun. 26, 2020, which claims the benefit of and priority to U.S. Provisional Patent Application No. 62/866,846 filed Jun. 26, 2019, all of which are hereby incorporated by reference in their entireties.

BACKGROUND

The present invention relates generally to the field of treatment for clogged glands and/or partially clogged glands of the eye, and particularly, to a thermal compress for providing heat to an eye region for treating the clogged glands.

Many people experience dry eye syndrome. One of the causes of dry eyes is that the oil glands of the eyes, known as the Meibomian glands, become clogged. One condition that relates to a blockage or other abnormality of the Meibomian glands is referred to as Meibomian gland dysfunction (MGD). For a person with MGD, the Meibomian glands do not secrete enough oil into the eyes. When tears are inside the eye, they will quickly evaporate unless there is a layer of oil on top. The oil prevents evaporation of tears and also helps lubricate the eyes. Because the tears then evaporate too quickly, MGD is associated with dry eye syndrome. MGD also relates to an eyelid problem called blepharitis which causes inflammation of the eyelids.

A common recommendation from medical professionals for treatment of dry eye syndrome and/or blepharisis is to take a fabric eye mask, wet it, and then heat it in the microwave for 20 seconds before applying to the eye region to unclog the glands. There are two primary issues associated with this method. First, the heat very quickly dissipates and becomes ineffective. Second, the fabric on the mask is not directly focused on the target area, but rather heats up the entire general eye area including the eyebrows and upper cheeks.

There is, therefore, a need for a more effective treatment of MGD, dry eye syndrome, blepharitis, and/or any other condition that involves clogged glands in the eye region.

SUMMARY OF THE INVENTION

A system for treating clogged glands of the eye includes a heated eye mask, an electrical cord, and a controller. The heated eye mask includes an outer layer of surface material, an inner layer of surface material, and a graphene heating element. The outer layer of surface material is configured to be positioned away from an eye region of a user. The inner layer of surface material is configured to contact the eye region of the user. The graphene heating element is disposed between the outer layer of surface material and the inner layer of surface material in a therapeutic region of the heated eye mask. The therapeutic region of the heated eye mask is a portion of the heated eye mask configured to cover only an area of the eye region of the user extending along the Meibomian glands of the eye. An electrically insulating cover encapsulates the graphene heating element. A thermally conductive material is in contact with the graphene heating element and the inner layer of surface material to evenly distribute heat across the therapeutic region of the heated eye mask. The electrical cord is coupled to the heated eye mask for providing power to the heated eye mask. The controller is provided on the electrical cord for controlling the heated eye mask. The controller includes a temperature control to control the heated eye mask to heat to one of at least four pre-set temperature levels.

Another embodiment relates to a system for treating clogged glands of an eye. The system includes a heated eye mask, an electrical cord coupled to the heated eye mask for providing power to the heated eye mask, and a controller provided on the electrical cord for controlling the heated eye mask. The controller comprises a temperature control to control the heated eye mask to heat to one of at least four pre-set temperature levels.

DETAILED DESCRIPTION

Figure 1:
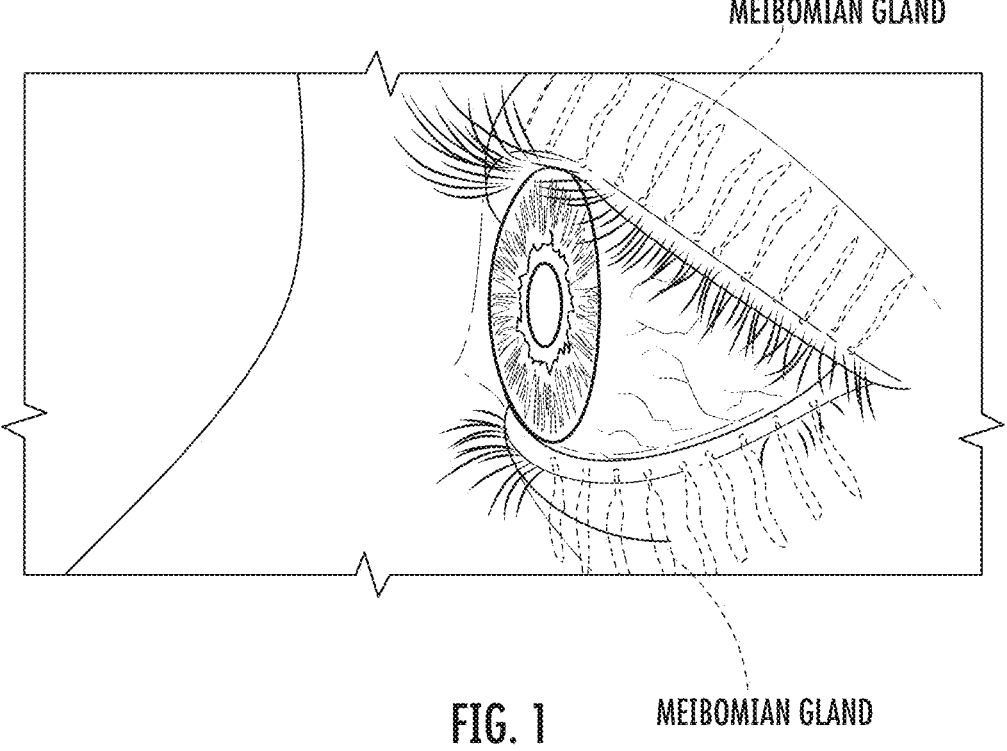
FIG. 1 depicts the human eye showing the Meibomian glands.
Figure 2:
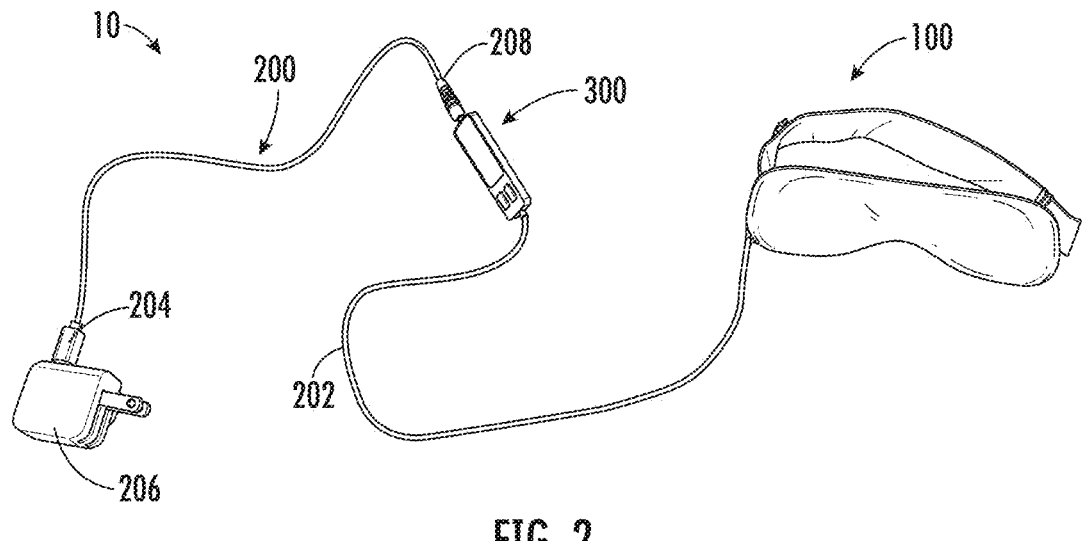
FIG. 2 shows a system for treatment of clogged glands of the eye.

One cause of dry or irritated eyes is blockage of the Meibomian glands of the eyes. The Meibomian glands are depicted in FIG. 1. The Meibomian glands provide oils to the eyes for protection and moisture. FIG. 2 depicts a system 10 for treating clogged glands of an eye, such as the Meibomian glands, by providing heat to melt the oils in the glands, and therefore, unclog the glands.

As shown in FIG. 2, the system 10 includes a heated eye mask 100, a power source 200, and a controller 300. The heated eye mask 100 is configured to be worn by a user by positioning and securing the mask 100 over the user's eye region. The power source 200 provides power to the eye mask 100 for heating the eye mask 100 during a treatment session. The controller 300 is coupled to the power source 200 to control the time of the treatment session and/or the temperature provided by the eye mask 100 during the treatment session.

Figure 3:
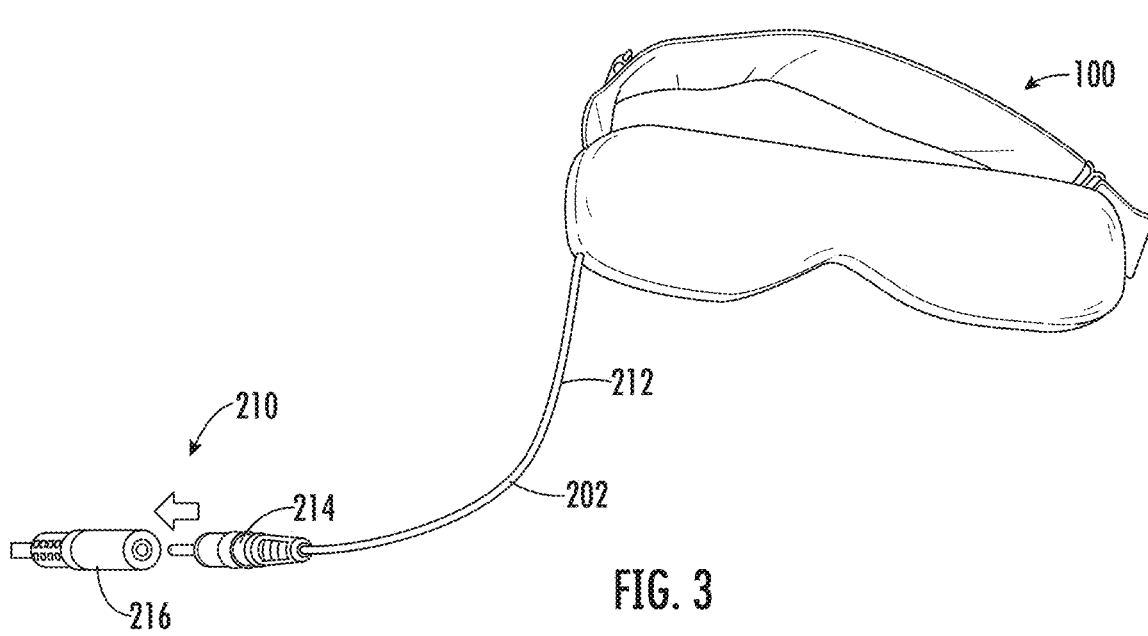
FIG. 3 shows an electric heated eye mask of the system of FIG. 2 having an alternative power source configuration.

The power source 200, shown in FIG. 2, is an electrical cord 202 with a USB interface 204 at its distal end. In such embodiments, the USB interface 204 is configured to be coupled to any USB power device such as a 5V adapter 206 for a wall outlet, a battery pack, a personal computer, a USB power hub, etc. The power source 200 can have a USB interface on the proximal end. In such embodiments, the USB interface is configured to be coupled to a USB receiver in the controller 300. The power source 200 can have a DC plug 208, as shown in FIG. 2, on the proximal end. In such embodiments, the DC plug is configured to be coupled to a DC port in the controller 300. In an alternative embodiment, shown in FIG. 3, there is a disconnectable portion 210 along the electrical cord 202. Specifically, a power connector 212 extends from the eye mask 100. The power connector 212 is a lead wire having a socket 214 at its distal end. The socket 214 is configured to receive a DC plug 216 which continues to an interface, such as the USB interface 204, for plugging into a power supply.

Figure 4:
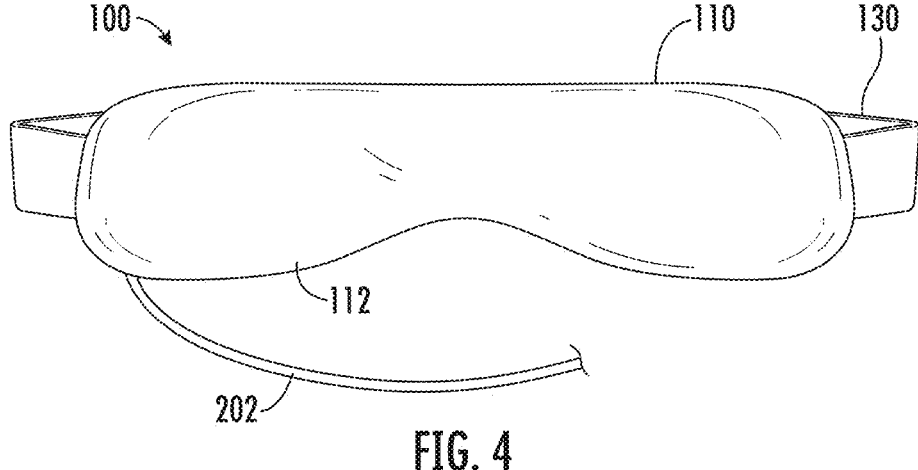
FIG. 4 shows an electric heated eye mask for treatment of clogged glands of the eye.
Figure 5:
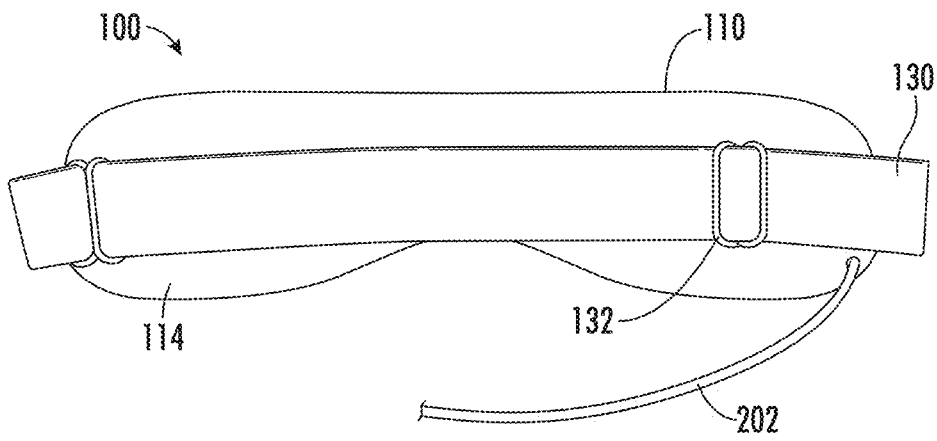
FIG. 5 is an alternative view of the electric heated eye mask shown in FIG. 4.

Referring to FIGS. 4-5, the heated eye mask 100 is shown in greater detail. FIG. 4 is a front view of the heated eye mask 100, showing an outside of the mask 100 that would face away from a user. FIG. 5 is a rear view of the heated eye mask 100, showing an inside of the mask 100 that would be in contact with the eye region of the user. As shown, the heated eye mask 100 includes a mask body 110 and an adjustable strap 130, with the electrical cord 202 extending from the mask body 110. The mask body 110 is made up of a first layer of surface material 112 configured to be positioned away from the eye region of the user, and a second layer of surface material 114 configured to be in contact with the eye region of the user. The first layer 112 and second layer 114 of surface material are stitched, or otherwise attached, together along an outer perimeter to form the mask body 110. The mask body 110 is also coupled to an adjustable strap 130. In some embodiments, the adjustable strap 130 is elastic. In some embodiments, the adjustable strap 130 is adjustable by way of one or more length adjustment mechanisms 132.

Figure 6A:
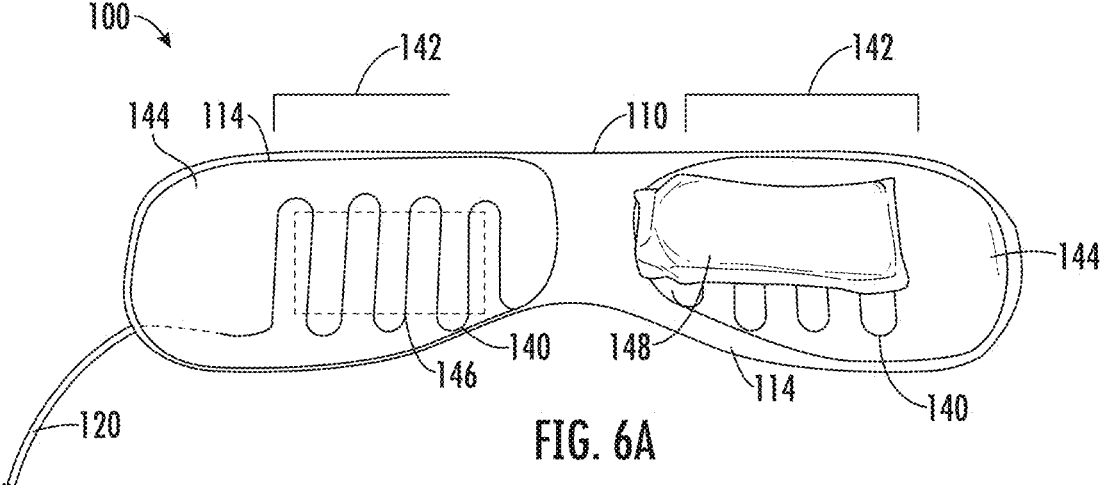
FIG. 6A is a view of the arrangement of the internal elements of the electric heated eye mask of FIG. 4.
Figure 6B:
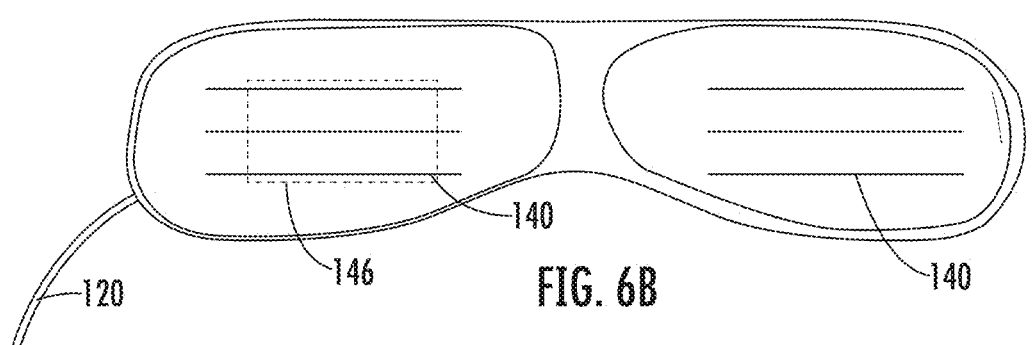
FIG. 6B is an alternative view of the arrangement of the internal elements of the electric heated eye mask of FIG. 4.

FIGS. 6A-6B show an arrangement of internal elements of the mask body 110 with the first layer of surface material 112 (the outer facing layer) removed. As shown, the mask body 110 includes a heating element 140, also referred to as a heating element assembly 140, positioned between the first layer of surface material 112 and the second layer of surface material 114. In the embodiments shown, the heating element 140 is a flexible fiber, such as a wire. The wire may be a metal fiber heating wire. The wire may be made of nickel-chromium (nichrome). In the embodiment shown in FIG. 6A, the heating element 140 is arranged in a sinusoidal shape. It is to be understood, however, that the heating element can be arranged in any shape or form in order to provide heat to a target area of the mask body 110, such as any number of horizontal lines, such as the three horizontal lines shown in FIG. 6B, any number of vertical lines, a zigzag pattern, etc. The heating element 140 is positioned in a therapeutic region on both sides (right and left eye) of the mask body 110. The therapeutic region includes two therapeutic zones 142A, 142B. A first therapeutic zone 142A is aligned with the Meibomian glands of the right eye and a second therapeutic zone 142B is aligned with the Meibomian glands of the left eye, with a gap between the two therapeutic zones 142A, 142B. In this way, heat is targeted to a certain area over each eye, particularly, the area along the eyelids where the Meibomian glands are found. This targeted therapy that is achieved by positioning the heating element 140 specifically in the therapeutic region provides a more effective treatment for blockage of the Meibomian glands than widespread heat distribution across the entire eye region.

In some embodiments, the heating element 140 is stitched to one or more intermediate layers 144 that are positioned or attached (e.g., by stitching or adhesive) between the first layer of surface material 112 and the second layer of surface material 114. In such embodiments, the heating element 140 may be positioned and stitched in between two intermediate layers 144. The intermediate layer(s) 144 assist in maintaining the heating element 140 in its desired shape and positioned in the therapeutic region 142. The material of the intermediate layer(s) 144 is any material having adequate strength and structure to hold the heating element 140 in position. In some embodiments, there is a piece of thermally conductive material 146 positioned between second layer of surface material 114 and the heating element 140 (i.e., towards the user's eye) in both therapeutic regions 142A, 142B. The thermally conductive material 146 is configured to evenly disperse the heat generated by the heating element 140. The material is preferably a conductive fabric made from, coated, or blended with conductive metals. In some embodiments, a base material, such as cotton, wool, polyester, or nylon, is coated or blended with the conductive metal. The conductive metal may be gold, carbon, titanium, nickel, silver, or copper, for example. The thermal conductive material 146 is preferably a small piece of material that is sized and configured to cover only the therapeutic region 142, therefore further assisting in the targeted therapy to only the area of the eye in which the Meibomian glands are found. To this end, in some embodiments, an additional blocking material 150, for example, a thermal blocking material, may be added in the area of the bridge of the user's nose which prevent the spread of heat between the therapeutic regions 142A, 142B over the right and left eyes.

Still referring to FIG. 6A, in some embodiments, a pillow 148 is provided between the first layer of surface material 112 and the heating element 140 on both sides of mask body 110 (i.e., over each eye). The pillow 148 is configured to apply additional pressure to the heating element 140 to urge the heating element 140 towards the eye socket of the user. Thus, providing an additional therapeutic benefit of maintaining heat and contact throughout the therapy session. In some embodiments, the pillow 148 is made of a polyester material. In some embodiments, the mask body 110 is filled with a flexible, filler material (not shown) to soften the mask body 110 and allow flexibility of the mask to form to the user's eye region. In some embodiments, the filler material is a non-synthetic material which will not heat up when exposed to the heating element 140 (or only minimally) and will also not emit any chemicals or other harmful elements when exposed to heat. For example, the filler material may be flax seed. In addition to being non-synthetic, flax seed also comprises very small seed elements which easily contour to the user's eye region for a comfortable fit. Other types of filler material may be used, such as other materials containing small elements (i.e., beads or seeds) or a soft material (i.e., cotton, polyester, feathers, etc.)

Figure 7:
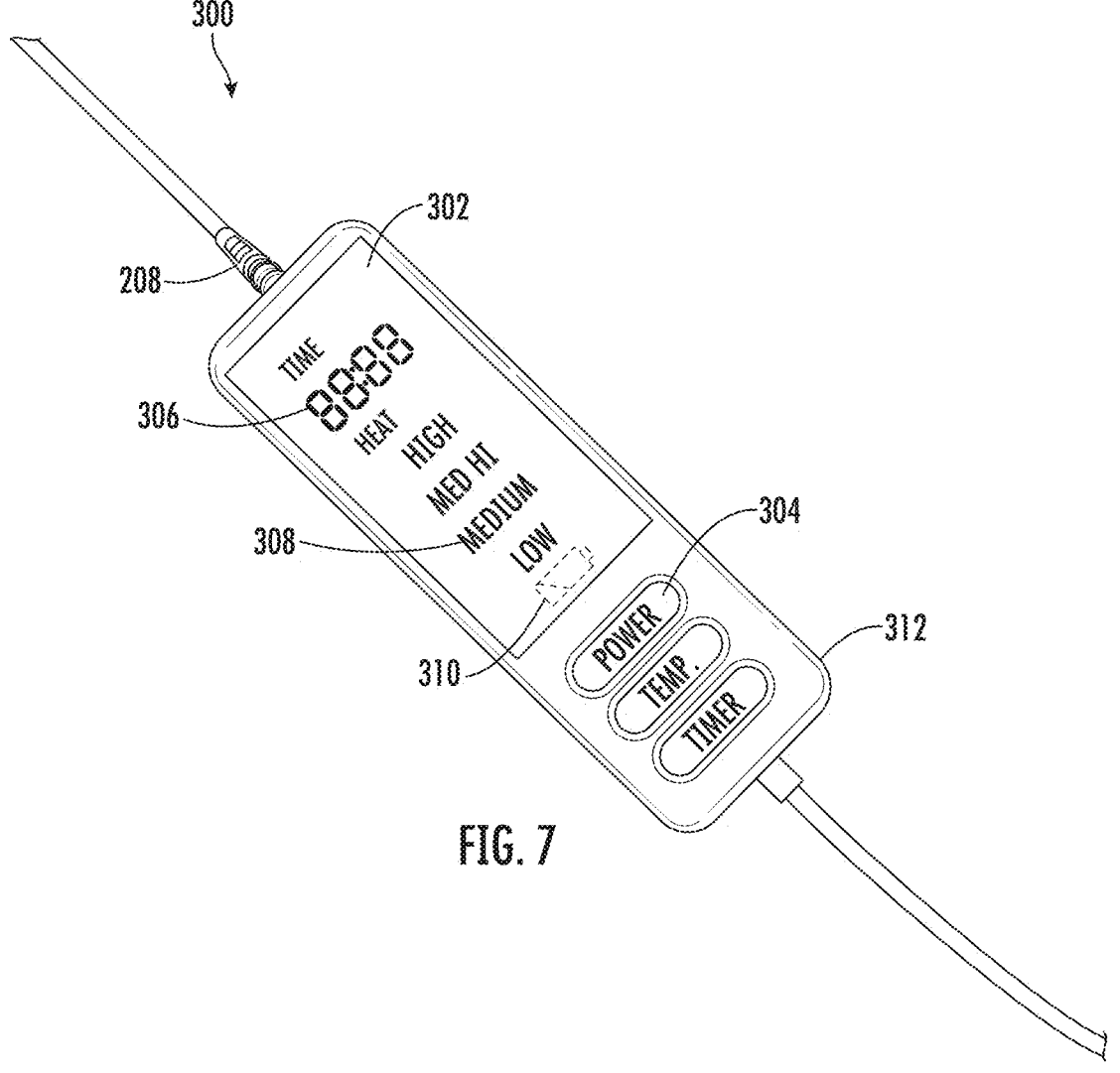
FIG. 7 depicts a heat controller for use with an electric heated eye mask.

FIG. 7 depicts a controller 300 for controlling the time and temperature settings of the therapy session. In the embodiment shown, the controller 300 includes a display portion including a display 302, an input portion including one or more buttons, switches, or other type of input mechanism 304, an integrated circuit, a battery 310, and a housing 312. The integrated circuit can be configured to receive inputs from the input mechanism 304 and provide a display via the display 302. The integrated circuit can provide power to the electrical cord 202 based on the received input from the input mechanism 304. In some embodiments, the display is a touch screen display, and in such cases the display 302 and the input mechanism 304 are a unitary element. In the embodiment shown, the display 302 provides a digital output 306 of the time of the therapy session (it may show time remaining or time elapsed) and an indicator 308 of the temperature setting. The time of the therapy session may be a specific length of time selected by the user, or the controller may allow for selection of one of a plurality of pre-set lengths of time. For example, in some embodiments, the preset lengths of time may start at minimum time (for example, at 10 minutes, 20 minutes, etc.) and increase in two minute intervals. In other embodiments, there may be fewer preset options such as 10 minutes, 15 minutes, 20 minutes, 25 minutes, and 30 minutes. For best results, it is recommended that a user wear the mask twice a day for at least 8 minutes.

In the embodiment shown in FIG. 7, the indicator 308 of the temperature setting is lighting element which illuminates one of four preset temperature settings: low (125)—every second (every other second), medium (135)—2 seconds, medium high (140)—cuts every 3 seconds, or high (145)—heat on continuously. In some embodiments, the low setting provides a temperature of approximately 125 degrees Fahrenheit, the medium setting provides a temperature of approximately 135 degrees Fahrenheit, the medium high setting provides a temperature of approximately 140 degrees Fahrenheit, and the high setting provides a temperature of approximately 145 degrees Fahrenheit. The preset temperatures are achieved by regulating the power supplied to the heating element. For example, to achieve the high temperature, the power is maintained to the heating element 140 throughout the therapy session (e.g., 100% duty cycle). To achieve the medium high, medium, and low temperatures, the current is removed every three seconds (three seconds on, one second off) (e.g., 75% duty cycle), two seconds (two seconds on, one second off) (e.g., 66% duty cycle), or every other second (one second on, one second off) (e.g., 50% duty cycle), respectively.

In some embodiments, there may be fewer or more preset temperature settings, or a user may be able to select a specific temperature in degrees for the therapy session. In a preferred embodiment, the temperature settings available to the user are in the range of 120 degrees Fahrenheit to 145 degrees Fahrenheit. The temperature settings may also be shown on the display in a digital format.

The input mechanism(s) 304 on the controller 300 allow a user to select the time and/or temperature settings of the therapy session. In the embodiment shown in FIG. 7, there is a power button, a temperature button, and a timer button. In other embodiments, there may be fewer or more input mechanism(s) such as additional "+" and a "−" buttons to allow a user to increase or decrease the time or temperature. Or, in another example, there may be a single button and a user toggles through an array of menu options in order to select the settings for the therapy session. In yet another example, there are two input mechanisms 304, one for the time setting and the other for the temperature setting.

The battery 310 can be any suitable rechargeable battery. For example, the battery 310 can be a lead-acid battery, a nickel-cadmium battery, nickel-metal hydride battery, etc. The battery 310 can be charged by plugging into the power source 200. Advantageously, the battery 310 allows the user to utilize the mask 100 without needing to be plugged into an outlet, or carry an external battery (e.g., battery pack, laptop).

The housing 312 can be of any suitable material (e.g., polyethylene, polypropylene, ABS). The display 302, input mechanisms 304, integrated circuit, and battery 310 can be maintained within the housing 312. The housing 312 can have an elongated rectangular shape. This may be beneficial as the elongated rectangular shape can provide the user an ergonomic grip of the controller 300.

Figure 8:
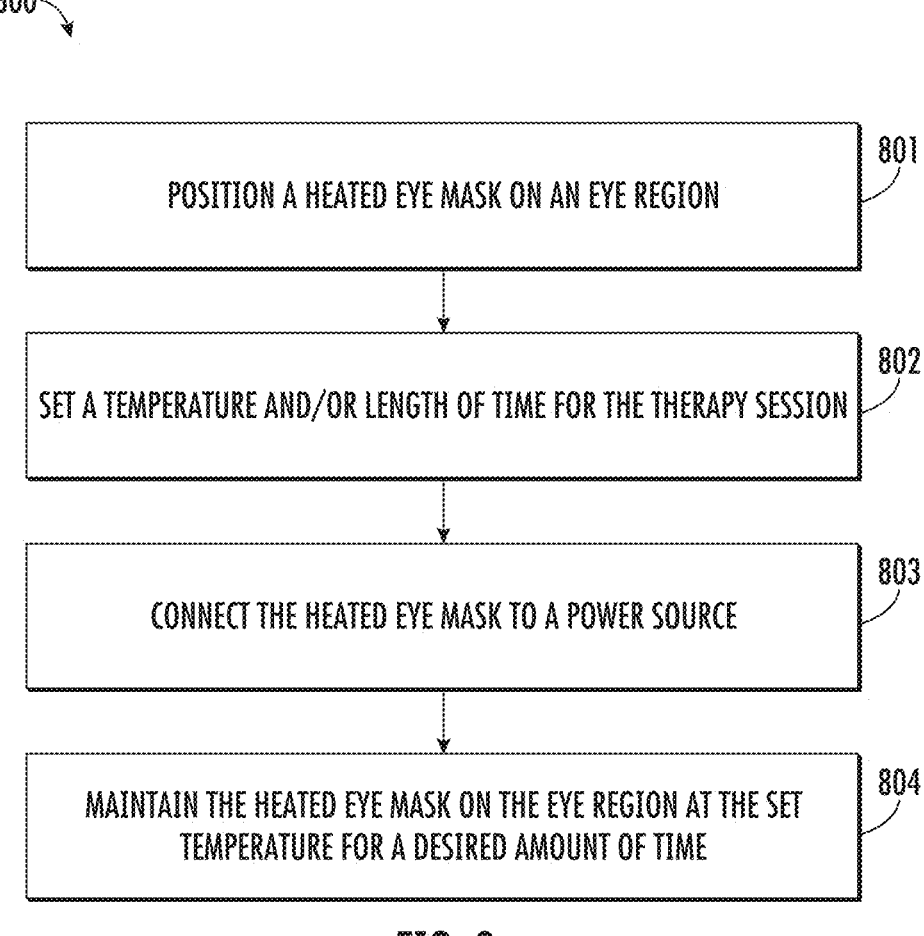
FIG. 8 is a flowchart depicting a method for treating clogged glands of the eye.

FIG. 8 depicts a method 800 for using the heated eye mask system 10 for treating clogged glands of the eyes. In step 801, a user positions the heated eye mask 100 on the eye region. As described above, the design of the eye mask 100 provides for targeted therapy directly to the area of the eye in which the clogged glands may be found, for example, by the heating element 140 positioned particularly in the therapeutic region 142 and the pillow 148 to bias the heating element 140 towards the eye socket of the user. The user may position and secure the heated eye mask 100 on the eye region by placing the adjustable strap 130 over his or her head and adjusting the strap 130 for a secure fit. In step 802, which may be performed before or after positioning the eye mask 100 on the eye region, the user selects the therapy session parameters, such as the length of time and temperature settings for the therapy session. In step 803, the heated eye mask 100 is connected to a power source 200, such as a standard wall outlet with a 5V plug adapter or to a battery pack. In step 804, the user maintains the heated eye mask 100 on the eye region for the desired length of time and temperature. The user may adjust the temperature or the time, as needed, during the therapy session. As mentioned above, for best results, it is recommended that a user wear the mask twice a day for at least 8 minutes.

Figure 9A:
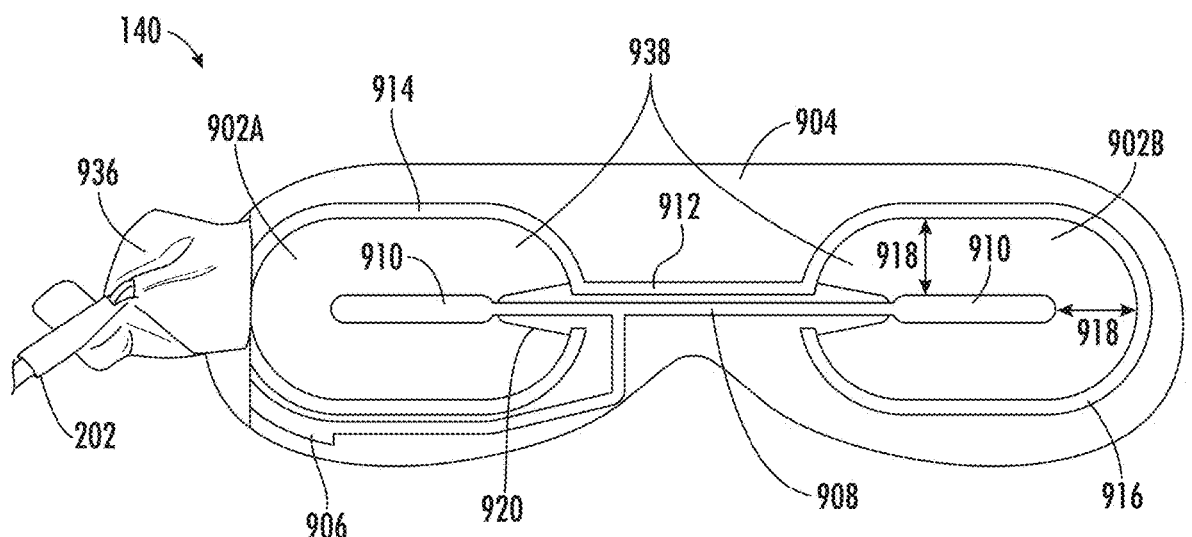
FIG. 9A shows a front side view of a heating element assembly.
Figure 9B:
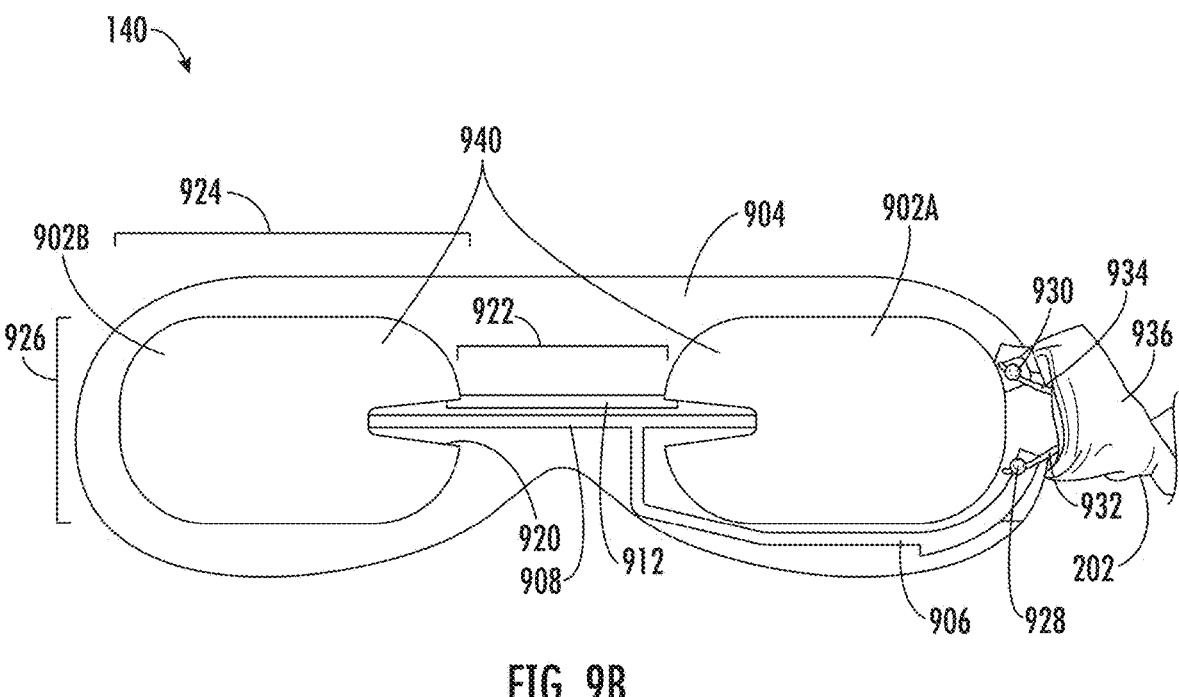
FIG. 9B shows a back side view of a heating element assembly.

Referring to FIGS. 9A and 9B, illustrate an exemplary embodiment of the heating element assembly 140 for use with an eye mask. FIG. 9A illustrates a front side of the heating element assembly 140 including a front surface 938 of a left graphene heating element 902A and a front surface 938 of a right graphene heating element 902B. FIG. 9B illustrates a back side of the heating element assembly 140 including a rear surface 940 of a left graphene heating element 902A and a rear surface 940 of a right graphene heating element 902B. The heating element 140, as described herein, is positioned in a therapeutic region covering both sides (right and left eye) of the mask body 110. The heating element assembly 140 is supplied with power by the electrical cord 202. In the embodiments shown in FIG. 9A and FIG. 9B, the heating element assembly 140 comprises two graphene heating elements 902 (e.g., left graphene heating element and right graphene heating element), a ground lead 906-910 (e.g., earth ground), a positive lead 912-916, and an electrically insulating cover 904 which encapsulates the two graphene heating elements 902, the ground lead 906-910, and the positive lead 912-916.

The graphene heating elements 902, as shown in FIG. 9B, can be a stadium shape (e.g., rectangle with rounded corners) having a separation distance of 922, a width of 924, and a height of 926. The graphene heating elements 902 can be shaped such that they imitate the shape of an eye and beneficially provide even heating of a right and a left eye of a user. For example, in one embodiment, the graphene heating elements 902 can be of an elliptical shape with a major axis of width 924 and a minor axis of a height 926. In some embodiments, the height 926 of the graphene heating elements 902 can range from 20 mm to 40 mm. In some embodiments, the height 926 can be 30 mm. In some embodiments, the width 924 of the graphene heating elements 902 can range from 30 mm to 70 mm. In some embodiments the width 924 can be 50 mm. The graphene heating elements 902 can have a gap 920 on central side of both a left graphene heating element 902A and a right graphene heating element 902B (e.g., on the left side of the right graphene heating element 902B, on the right side of the left graphene heating element 902A). The gap 920 can provide a channel for the ground contact leads 910 to pass through the first positive lead 914 and the second positive lead 916, on their respective sides, to prevent a short between the ground contact leads 910 and the positive leads 914 and 916. The gap 920 can be extend into the graphene heating element 902 for a distance equal to, or approximately equal to 25% of the width 924. The gap 920 can have an internal height (e.g., nearest the ground contact leads 910) equal to or approximately equal to 10% of the height 926. The gap 920 can have a distal height (e.g., furthest from the ground contact leads 910) equal to or approximately equal to 20% of the height 926.

The two heating elements can be separated by a separation distance 922. The separation distance 922 can be an average distance between the eyes of a common user. This can be beneficial as the graphene heating elements 902 can be positioned over the eyes of the user allowing for heating mask 100 to work more efficiently (e.g., so that heat is not wasted on the bridge of the nose). In some embodiments, the separation distance 922 of the two graphene heating elements 902 can range from 10 mm to 50 mm. In some embodiments, the separation distance 922 can be 30 mm. In some embodiments, a ratio of a surface area of the graphene heating elements 902 to a surface area of the surface material 114 can range from 2:3 to 1:4. In some embodiments, the ratio of the surface area of the graphene heating elements 902 to the surface area of the surface material 114 can be 2:5. The provided ratio of the surface area of the graphene heating elements 902 to the surface area of the surface material 114 can allow for the graphene heating elements 902 to cover the therapeutic regions 142 and further provide a secure and comfortable fit to the user.

In some embodiments, the graphene heating elements 902 can have a thickness ranging from 5 μm to 50 μm. In some embodiments, the graphene heating elements can have a thickness of 25 μm. In some embodiments, the resistance of the graphene heating elements 902 can range from 4 ohms to 6 ohms. In some embodiments, the resistance of the graphene heating elements 902 can be 5 ohms. The use of graphene for the graphene heating elements 902 in the heating element assembly 140 can beneficially provide the user with a consistent temperature across the graphene heating element 902. The user of the graphene for the graphene heating elements 902 in the heating element assembly 140 beneficially enables the heating element 140 to be heated and cooled more quickly than a resistive heating element due to the low heat capacity of graphene.

The ground lead 906-910 and positive lead 912-916 can be an electrically conductive material (e.g., copper). The ground lead 906-910 can comprise of a ground source lead 906, a ground bridge lead 908, and two ground contact leads 910, as described herein. The positive lead 912-916 can comprise of a first positive lead 914, a positive bridge lead 912, and a second positive lead 916, as described herein. The ground contact leads 910, the first positive lead 914, and the second positive lead 916 can be electrically coupled to the graphene heating elements 902 on the front surface 938 using any suitable method. For example, the ground contact leads 910, the first positive lead 914, and the second positive lead 916 can be coupled to the front surface 938 of the graphene heating elements 902 using a conductive adhesive, solder, heat forming, etc. In some embodiments, the positive lead 912-916 can provide a voltage ranging from 4.5 volts to 5 volts. In some embodiments, the positive lead 912-916 can provide a voltage of 5 volts. As described herein, the power supplied by the electrical cord 202 can be adjusted by the user utilizing the controller 300. In some embodiments, the controller 300 can provide four temperature settings. The temperature can be adjusted to suit the needs of the user. In some embodiments, the controller 300 can adjust the temperature of the heating elements by providing power at varying duty cycles (e.g., 50%, 66%, 75%, 100%). For example, a user can select a low temperature setting. Based on the selection, the controller 300 can provide 5 volts to the heating element assembly 140 via the electrical cord 202 with a duty cycle of 50% (e.g., one second on then one second off).

In some embodiments, the first positive lead 914 and the second positive lead 916 can connect with an outer edge of the graphene heating elements 902. In the illustrated embodiment, the positive leads 914 and 916 can be electrically coupled to a majority of the circumference of the graphene heating elements 902. The majority of the circumference of the graphene heating elements 902 can be the circumference of the graphene heating elements excluding the gap 920 (e.g., approximately 95% of the total circumference). The first positive lead 914 and the second positive lead 916 can cover the circumference of the graphene heating elements 902 without covering an internal surface of the gap 920. This gap 920 and the break in the first positive lead 914 and the second positive lead can allow for the ground contact leads 910 to contact the center of the graphene heating element without causing a short between the ground lead 906-910 and the positive lead 912-916. The first positive lead 914 is connected to the second positive lead 916 by the positive bridge lead 912. The positive bridge lead 912 can be located in a central portion of the mask body 110 that extends over the bridge of the nose of the user.

As shown in FIG. 9B, a positive wire 934 from the electrical cord 202 can be electrically coupled to a positive terminal 930. The positive terminal 930 is electrically coupled to the first positive lead 914. This connection provides the positive lead 912-916 with power supplied by the electrical cord 202. In some embodiments, the positive wire 934 can be electrically connected to the positive terminal 930 by solder, conductive adhesive, mechanical coupling (e.g., clamp, screw socket terminal). The use of a mechanical coupling in the positive terminal 930 can be beneficial as it can allow for a simple reconnection if the positive wire 934 and the positive terminal 930 become disconnected.

In some embodiments, the ground contact leads 910 can be connected to the center of the graphene heating elements 902. The ground contact leads 910 can be of an elongated stadium shape with a height approximately 12.5% of the height 926 and a width approximately 50% of the width 924 The ground contact leads 910 can be electrically connected to the first positive lead 914 and the second positive lead 916 through the graphene heating elements 902 such that an electrical current can pass through the graphene heating elements 902. The ground contact leads 910 can be shaped such that there is a constant lead distance 918 between the first positive lead 914 or second positive lead 916 and the ground contact leads 910 through the graphene heating elements 902. As such, the distance between the ground lead 906-910 and the positive lead 912-916 is not constant at the gap 920 as the leads are not connected through the graphene heating elements 902 at the gap 920. The constant lead distance 918 can be beneficial as it provides uniform heating throughout the graphene heating elements 902. The ground contact leads 910 can be connected to a ground bridge lead 908 that connects the two ground contact leads 910 with the ground source lead 906. The ground bridge lead 908 can be located in a central portion of the mask body 110 that extends over the bridge of the nose of the user and can be configured to run in parallel with the positive bridge lead 912.

As shown in FIG. 9B, a ground wire 932 from the electrical cord 202 can be electrically coupled to a ground terminal 928. The ground terminal 928 is electrically coupled to the ground source lead 906. This connection provides the ground lead 906-910 with a ground (e.g., earth ground) supplied by the electrical cord 202. In some embodiments, the ground wire 932 can be electrically connected to the ground terminal 928 by solder, conductive adhesive, mechanical coupling (e.g., clamp, screw socket terminal). The use of a mechanical coupling in the ground terminal 928 can be beneficial as it can allow for a simple reconnection if the ground wire 932 and the ground terminal 928 become disconnected. The ground lead 906-910 can be an earth ground, common ground, etc. It should be appreciated that the ground lead 906-910 and the positive lead 912-916 can be switched such that the ground lead 906-910 is held at a positive voltage and the positive lead 912-916 is held at a ground voltage.

The positive terminal 930 and the ground terminal 928 are located on the back side of the heating element assembly 140 away from the user's face and eyes. This can be beneficial as it prevents any discomfort that may be caused by the terminals. The ground terminal 928, positive terminal 930, ground wire 932, and the positive wire 934 can be wrapped in an electrically insulating sheathing 936 (e.g., electrical tape) to insulate the exposed wires and terminals preventing the insulated components from shorting, causing a shock, or becoming disconnected.

The electrically insulating cover 904 can be of any electrically insulating material (e.g., polymide). The electrically insulating cover 904 mostly encapsulates and insulates the graphene heating elements 902, the positive lead 912-916 and the ground lead 906-910. The electrically insulating cover 904 can have an absence of material surrounding the positive terminal 930 and the ground terminal 928 allowing an electrical coupling between the ground lead 906-910 and the ground terminal 928 and the positive lead 912-916 and the positive terminal 930. The electrically insulating cover 904 can further prevent the positive lead 912-916 and ground lead 906-910 from shorting, and hold the graphene heating elements 902, positive lead 912-916, and ground lead 906-910 in place. In some embodiments, the electrically insulating cover 904 is stitched to one or more intermediate layers 144 that are positioned or attached (e.g., by stitching or adhesive) between the first layer of surface material 112 and the second layer of surface material 114. In such embodiments, the electrically insulating cover 904 may be positioned and stitched in between two intermediate layers 144. The intermediate layer(s) 144 assist in maintaining the heating element assembly 140 in its desired shape and positioned in the therapeutic region 142.

As shown in FIGS. 2, 6A, 6B, 9A, and 9B, the system 10 includes a heated eye mask 100, a power source 200, and a controller 300. The heated eye mask 100 is configured to be worn by a user by positioning and securing the mask 100 over the user's eye region. The power source 200 provides power to the eye mask 100 for heating the eye mask 100 during a treatment session. The controller 300 is coupled to the power source 200 to control the time of the treatment session and/or the temperature provided by the eye mask 100 during the treatment session. Based on the temperature setting as selected by the user via the controller 300, power is sent to the heating element assembly 140 with a particular duty cycle (e.g., 50%, 75%, 100%). The heating element assembly 140 can then receive a positive voltage and a ground voltage from the controller 300 via the electrical cord 202. The graphene heating elements 902 can emit heat based on the voltage difference (e.g., 5 volts) between a positive lead 912-916 mostly surrounding the graphene heating elements 902 and ground contact leads 910 centered in the graphene heating elements 902. The heat generated by the graphene heating elements 902 can then be transferred through the thermally conductive material 146 of the mask body 110 and applied to the therapeutic regions 142A and 142B which align with the Meibomian glands of the right and left eye, respectively.

As utilized herein with respect to numerical ranges, the terms "approximately," "about," "substantially," and similar terms generally mean$+/-10\%$ of the disclosed values. When the terms "approximately," "about," "substantially," and similar terms are applied to a structural feature (e.g., to describe its shape, size, orientation, direction, etc.), these terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein.

A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the assembly as shown in the various exemplary embodiments is illustrative only. Additionally, any element disclosed in one embodiment may be incorporated or utilized with any other embodiment disclosed herein. For example, the heating element assembly 140 of the exemplary embodiment described herein may be incorporated in the mask body 110 of the exemplary embodiment described herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A heated eye mask for treating clogged glands of an eye, the eye mask comprising:
    a mask body, the mask body comprising: an outer layer configured to be positioned away from an eye region of a user and an inner layer configured to contact the eye region of the user;
    a heating element disposed between the outer layer and the inner layer, the heating element assembly comprising:
    a left heating element having a circumference, a front surface facing the inner layer, and a rear surface facing the outer layer;
    a right heating element having a circumference, a front surface facing the inner layer, and a rear surface facing the outer layer;
    a first lead electrically coupled with the front surface of the left graphene heating element around a majority of the circumference of the left graphene heating element and the first lead electrically coupled with the front surface of the right graphene heating element around a majority of the circumference of the right graphene heating element;
    a second lead electrically coupled with the front surface of the left graphene heating element, the second lead having a first contact lead located in a center area of the left graphene heating element, and the second lead electrically coupled with the front surface of the right graphene heating element, the second lead having a second ground contact lead located in a center area of the right graphene heating element.

2. The eye mask of claim 1, further comprising a power source comprising a first terminal and a second terminal, wherein the first terminal is electrically coupled to the first lead and the second terminal is electrically coupled to the second lead.

3. The eye mask of claim 1, wherein the mask body is filled with flax seed between the outer layer and the inner layer.

4. The eye mask of claim 1, wherein the heating element is disposed in a therapeutic region of the eye mask, wherein the therapeutic region of the eye mask is a portion of the eye mask configured to cover only an area of the eye region of the user extending along the Meibomian glands of the eye.

5. The eye mask of claim 1, further comprising an electrically insulating cover encapsulating the left heating element, the right heating element, the first lead, and the second lead.

6. The eye mask of claim 1, further comprising:
    an electrical cord coupled to the mask body for providing power to the heating element; and

a controller coupled to the electrical cord for controlling the heating element, wherein the controller comprises a temperature control to control the heating element to heat to one of at least four pre-set temperature levels.

7. The eye mask of claim 6, wherein the electrical cord comprises a USB interface for connecting with a power supply.

8. The eye mask of claim 7, wherein the power supply is a USB adapter for plugging into a wall power socket.

9. The eye mask of claim 6, wherein the controller comprises a timer.

10. The eye mask of claim 9, wherein the timer is configured to control the heating element to provide heat for a specified period of time, wherein the specified period of time is adjustable.

11. The eye mask of claim 10, wherein the specified period of time is at least 8 minutes.

12. The eye mask of claim 6, wherein the at least four pre-set temperature levels are set by the controller providing power at a duty cycle of 100%, a duty cycle of 75%, a duty cycle of 66%, and a duty cycle of 50%.

13. The eye mask of claim 6, wherein the at least four pre-set temperature levels comprise 125 degrees Fahrenheit, 135 degrees Fahrenheit, 140 degrees Fahrenheit, and 145 degrees Fahrenheit.

* * * * *